United States Patent [19]

van de Mond et al.

[11] 4,250,118

[45] Feb. 10, 1981

[54] PROCESS FOR THE PREPARATION OF CYCLOHEXANONE

[75] Inventors: Theodorus J. van de Mond; Hubertus J. A. Delahaye, both of Geleen, Netherlands

[73] Assignee: Stamicarbon, B.V., Geleen, Netherlands

[21] Appl. No.: 31,871

[22] Filed: Apr. 20, 1979

[30] Foreign Application Priority Data

Apr. 29, 1978 [NL] Netherlands .......................... 7804667

[51] Int. Cl.³ ............................................. C07C 45/65
[52] U.S. Cl. .................................... 568/338; 585/266;
568/826; 422/189; 568/376; 568/357; 568/360;
568/361; 568/366
[58] Field of Search ...................... 260/586 P; 585/266

[56] References Cited

U.S. PATENT DOCUMENTS

| | | | |
|---|---|---|---|
| 2,083,877 | 6/1937 | Steck et al. | 260/586 P X |
| 3,027,410 | 3/1962 | Poehler et al. | 260/586 P |
| 3,318,965 | 5/1967 | Hutto et al. | 585/266 |
| 3,767,719 | 10/1973 | Colvert et al. | 585/266 |

FOREIGN PATENT DOCUMENTS 939613 10/1963 United Kingdom .

*Primary Examiner*—Bernard Helfin
*Attorney, Agent, or Firm*—Cushman, Darby & Cushman

[57] ABSTRACT

An improved process for the preparation of cyclohexanone from benzene. Benzene is hydrogenated in a gaseous phase in a hydrogenation zone to form cyclohexane; cyclohexane is oxidized in a liquid phase to form a mixture containing cyclohexanol and cyclohexanone; and cyclohexanone is separated from this mixture and is catalytically dehydrogenated to form cyclohexanone and a hydrogen containing gas. The resulting hydrogen containing gas is introduced into a washing zone wherein it is washed with cyclohexane or benzene and the hydrogen gas thus purified is fed into the hydrogenation zone.

5 Claims, 1 Drawing Figure

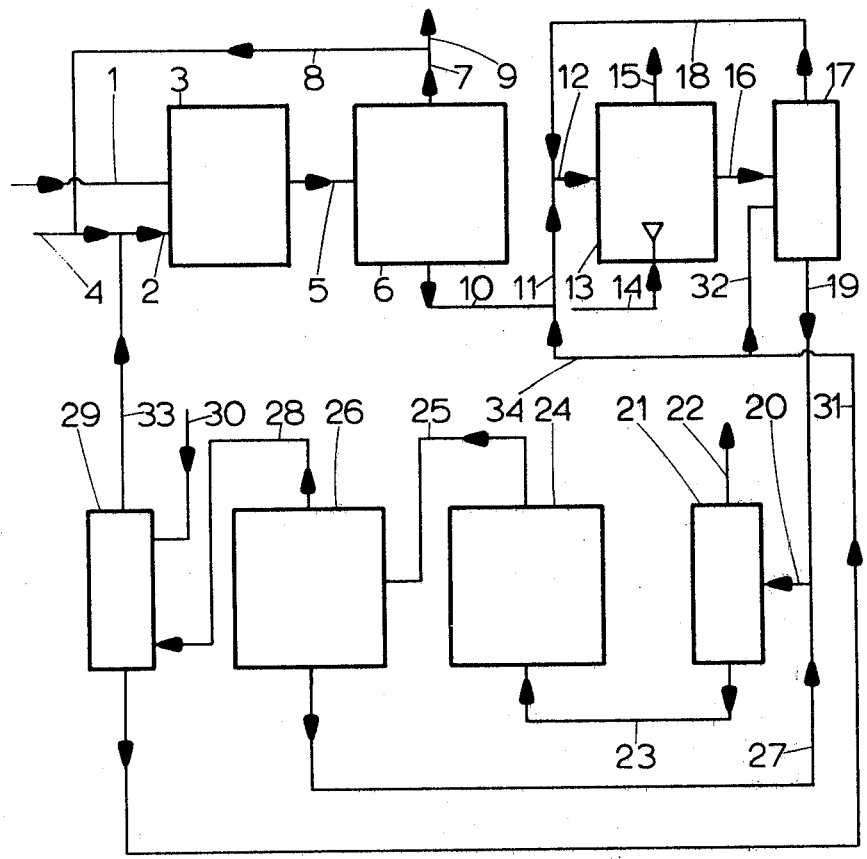

PROCESS FOR THE PREPARATION OF CYCLOHEXANONE

BACKGROUND OF THE INVENTION

This invention relates to a process for the preparation of cyclohexanone. Processes are known in which benzene is hydrogenated in a gaseous phase into cyclohexane, the cyclohexane is oxidized in a liquid phase with oxygen or a gas containing oxygen to form a mixture containing cyclohexanol, and the resulting cyclohexanol is catalytically dehydrogenated into cyclohexanone. Hydrogen gas is formed as a by-product in the dehydrogenation step, but is generally of a quality unsuitable for chemical synthesis because of the presence of organic impurities. Even after being cooled to remove the impurities to the extent possible by condensation, the hydrogen gas can still be used only as a fuel gas with a very low calorific value.

Attempts have been made in other processes to use hydrogen gas liberated during a dehydrogenation step in a hydrogenation step. For instance in British Patent Specification No. 939,613, a process for the preparation of phenol is disclosed wherein benzene is hydrogenated into cyclohexane, the cyclohexane is oxidized into a mixture of cyclohexanol and cyclohexanone, and this mixture is dehydrogenated into phenol and hydrogen. Although this hydrogen is thereafter used in the hydrogenation step, it is impossible to efficiently effect the benzene hydrogenation in a gaseous phase using this contaminated hydrogen, particularly with a metal catalyst from the platinum group, inasmuch as the catalyst very soon looses its activity. This is most probably due to the presence of organic impurities in the hydrogen gas coming from the cyclohexanol dehydrogenation step.

It is very desirable, however, to be able to effect the benzene hydrogenation in a gaseous phase, and preferably with a metal catalyst from the platinum group. Under such conditions a high rate of reaction can be obtained with a very high yield of cyclohexane, and furthermore benzene containing sulphur can readily be processed. It is therefore an object of the present invention to provide a process for the preparation of cyclohexanone wherein the contaminated hydrogen gas liberated in the dehydrogenation step can be simply and sufficiently purified for use in the gas phase benzene hydrogenation step.

BRIEF DESCRIPTION OF THE INVENTION

According to the invention, cyclohexanone is prepared by a process in which benzene is hydrogenated in a gaseous phase into cyclohexane in a hydrogenation zone; the cyclohexane is oxidized in a liquid phase in an oxidation zone, with a gas containing molecular oxygen to form a mixture containing cyclohexanol; the resulting cyclohexanol is dehydrogenated catalytically into cyclohexanone and hydrogen in a dehydrogenation zone; and cyclohexanone is separated from the resulting mixture of cyclohexanone and unconverted cyclohexanol and hydrogen. According to the improvement of the present invention, the gas phase resulting from the dehydrogenation step after separation of cyclohexanone and unconverted cyclohexanol, which gas phase primarily consists of hydrogen, is washed in a washing zone with a washing liquid of cyclohexane and/or benzene, and the washed hydrogen containing gas thus obtained is fed into the hydrogenation zone wherein it is utilized to provide at least a portion of the hydrogen necessary to hydrogenate the benzene.

This process offers a very considerable saving of hydrogen gas used for the benzene hydrogenation, while at the same time retaining the long useful life of the hydrogenation catalyst, as well as a high reaction rate and a high hydrogenation yield. Also extraneous substances are not introduced into the system. The washing liquid can be purified again in a simple way, such as by distillation. Moreover, losses of cyclohexanone and cyclohexanol through the hydrogen vent are avoided.

The benzene hydrogenation is carried out in a gaseous phase, preferably in the presence of a metal catalyst selected from the platinum group. These metals include platinum itself, as well as osmium, iridium, ruthenium, rhodium and palladium. Preferably platinum is used. Other catalyst may also be used, such as nickel. The catalytically active metal is preferably supported on a carrier material, preferably aluminum oxide although other supporting materials, such as silica gel or kieselguhr, may be used.

The hydrogenation may be effected at a temperature of from about 150° to 400° C. and at a pressure of from about 0.5 to 5 MPa, although higher and lower pressures and temperatures may also be used. A very suitable embodiment of such a benzene hydrogenation has been described in British Patent Specification No. 1,104,275.

The cyclohexane oxidation may be effected in any known way, whether or not in the presence of a catalyst, such as a transition-metal compound, and with or without isolation of the intermediate cyclohexyl hydroperoxide. See, for instance, Stanford Research Institute reports 3 (1965), 3A (1971), 7 (1965), 307–319, and 7A (1968), 87–103. and U.S. Patent Nos. 2,497,349, 3,287,423, 3,316,302, 3,927,108, 3,937,735, 3,946,076 and 4,042,630.

This oxidation reaction is preferably carried out at a temperature of from about 120° to 190° C. The reaction pressure is not critical, but must be high enough to maintain a liquid phase in the oxidation zone. The degree of conversion based on cyclohexane fed into the oxidation zone will preferably range between about 1 and 12%. The oxygen containing gas used in this oxidation may be either air or air diluted with part of the vent gas. Other gases containing oxygen may also be used, but are less economical.

Cyclohexanone is separated in a known way from the resulting reaction mixture, which contains both cyclohexanone and cyclohexanol, such as by distillation in a distillation zone.

The cyclohexanol is then dehydrogenated into cyclohexanone and hydrogen in a dehydrogenation zone. This dehydrogenation may be effected in a known way, in either a gas or liquid phase, in the presence of a catalyst such as zinc or copper. See, for instance, Stanford Research Institute reports 7 (1965), 275–306, 7A (1968), 87–103 and 7B (1976), 182–186, British Patent Specification No. 739,263, 825,602 and 909,227 and U.S. Pat. No. 2,524,566. The resulting gas phase containing hydrogen is separated off. Cyclohexanone is recovered from the resulting liquid phase mixture of cyclohexanone and cyclohexanol, and the unconverted cyclohexanol is returned to the dehydrogenation zone.

The gas phase containing hydrogen from the dehydrogenation zone is contaminated with organic impurities, particularly cyclohexanone and cyclohexanol, and is washed with benzene or cyclohexane before it is fed into the benzene hydrogenation zone. Preferably cyclohexane is used as the washing liquid. This offers the additional advantage that the washing liquid effluent, that is, the used washing liquid leaving the washing zone, can be used directly as a feed for the cyclohexane oxidation step without previous purification. In fact, it has been found that the impurities present in this washing liquid effluent have an accelerating effect on the oxidation reaction, so that a higher through-put through the oxidation reactor is obtained. Also, if cyclohexane is used as the washing liquid, the effluent washing liquid can be processed together with the product mixture from the oxidation zone, preferably by distillation.

BRIEF DESCRIPTION OF THE DRAWING

The FIGURE schematically shows a preferred embodiment of a process for the preparation of cyclohexanone in which the improvement of the present invention is incorporated.

DETAILED DESCRIPTION OF A PREFERRED EMBODIMENT

With reference to the Figure, benzene vapor is fed through conduit 1, and a hydrogen-nitrogen mixture (80% by volume of hydrogen) is fed through conduit 2, into hydrogenation reactor 3. The hydrogen-nitrogen mixture of desired composition is obtained by mixing a hydrogen-nitrogen mixture that is relatively rich in nitrogen (supplied through conduits 4 and 8) with a hydrogen gas (supplied through conduit 33) that has been saturated with cyclohexane vapor at 10° C. in washing column 29. Hydrogenation reactor 3 contains platinum on aluminum oxide (0.3% of platinum) as a catalyst. The pressure in the hydrogenation reactor is about 3 MPa, and the peak temperature is about 400° C. If the starting benzene feed material contains sulphur, the hydrogenation may be carried out in two steps if desired, with a hydrogen-sulphide absorption step between the two hydrogenation steps as described in British Patent Specification No. 1,104,275.

The effluent gas mixture from the hydrogenation reactor flows through conduit 5 to condenser 6 wherein cyclohexane is made to condense. Part of the vent gas escaping from the condenser through conduit 7 is returned to hydrogenation reactor 3 through conduits 8 and 2, and part is vented through conduit 9. The vent gas contains about 22% by volume of hydrogen.

The condensate formed in condenser 6 consists of virtually pure cyclohexane with a benzene content of only about 0.01% by weight and a content of other impurities of less than 0.04% by weight, and is fed to oxidation reactor 13 through conduits 10, 11 and 12. In this oxidation reactor, the cyclohexane is oxidized in the presence of a cobalt napthenate catalyst in a liquid phase with air supplied through conduit 14, and at a temperature of about 160° C. and a pressure of about 0.9 MPa. If desired, however, the oxidation may be effected without a catalyst. The degree of conversion of the cyclohexane in the oxidation reactor amounts to about 4%. Cyclohexane is recovered by condensation in a known way from the vent gas leaving the oxidation reactor through conduit 15, and is returned to oxidation reactor 13 through a conduit not shown.

The liquid reaction mixture from the oxidation reactor flows through conduit 16 to distillation column 17 wherein cyclohexane is distilled off and returned to oxidation reactor 13 through conduits 18 and 12. The remaining cyclohexanone cyclohexanol mixture is passed to distillation column 21 through conduits 19 and 20.

In distillation column 21, cyclohexanone product is separated off and is discharged through conduit 22. The residual cyclohexanol may be further purified if necessary, and is passed through conduit 23 to dehydrogenation reactor 24 wherein it is dehydrogenated in a known way by means of a copper or zinc catalyst. This may e.g. be carried out at a temperature of from about 150° to 350° C. and a pressure of from about 0.01 to 1 MPa, but dehydrogenation is preferably effected in a gaseous phase at a temperature of about 250° C. and a pressure of 0.1 MPa. The resulting dehydrogenation reaction mixture, containing cyclohexanol, cyclohexanone and hydrogen, flows through conduit 25 to condenser 26 wherein the cylohexanone and unconverted cyclohexanol are condensed. This mixture of cyclohexanone and cyclohexanol is fed through conduits 27 and 20 to distillation column 21. The remaining gaseous phase from condenser 26, consisting primarily of contaminated hydrogen, passes through conduit 28 to washing column 29 wherein it is washed with a cyclohexane washing liquid supplied through conduit 30. The effluent washing liquid flows through conduits 31, 34, 11 and 12 to oxidation reactor 13, or all or a portion thereof may be fed through conduits 31 and 32 to distillation column 17. The washed, purified hydrogen is passed through conduits 33 and 2 to hydrogenation reactor 3.

Th operation of the invention will be further illustrated with reference to the following Examples I and II in comparison with comparative Example A.

EXAMPLE I

Contaminated hydrogen gas from the dehydrogenation of cyclohexanol into cyclohexanone and hydrogen gas is made to condense at a temperature of 10° C. The remaining hydrogen gas is still contaminated with about 4 mg of cyclohexanone and about 0.6 mg of cyclohexanol per liter of gas. This gas is fed, at the rate of 32.5 liters per hour, to the bottom of a washing column having an internal diameter of 15.5 mm and a length of 365 mm, and which is filled with glass beads of 3 mm cross-section. The top of the washing column is fed per hour with 200 ml of liquid cyclohexane having a temperature of 10° C. The effluent liquid is discharged from the bottom of the washing column. Purified hydrogen gas is discharged from the top.

At atmospheric pressure and a bed temperature of 160° C., the hydrogen thus purified is mixed with benzene in an amount of 40 ml per hour and is passed through a catalyst bed in a hydrogenation zone with 21.5 g (about 20 ml) of 0.3% by weight platinum on aluminum oxide.

Under these reaction conditions the benzene conversion is 61.7% after the reaction has become stable (after about 5 hours). After a reaction period of 96 hours the benzene conversion is 61.5%. the yield of cyclohexane is 99.8%.

EXAMPLE II

Example I is repeated, but less cyclohexane is fed into the washing column as a washing liquid, that is, 25 ml per hour. After the reaction has become stable (after about 5 hours), the benzene conversion is 62%. After a reaction period of 100 hours the benzene conversion is 56.5%. Hence the activity of the catalyst has dropped slightly. The yield of cyclohexane is 99.7%.

COMPARATIVE EXAMPLE A

Example I is repeated, but without washing or purifying the hydrogen gas resulting from the dehydrogenation of cyclohexanol before introducing it into the hydrogenation zone. After a reaction period of 97 hours the benzene conversion has fallen to 45.4% by weight, which indicates that the catalyst activity has become unacceptably low.

What is claimed is:

1. In a process for the preparation of cyclohexanone from benzene including:
   a hydrogenation zone wherein benzene is hydrogenated in a gaseous phase to form cyclohexane;
   an oxidation zone wherein cyclohexane is oxidized in a liquid phase to form a first mixture containing cyclohexanol and cyclohexanone;
   a cyclohexanone distillation zone wherein cyclohexanone is separated from a mixture containing cyclohexanone and cyclohexanol, leaving a cyclohexanol containing effluent; and
   a dehydrogenation zone wherein cyclohexanol is catalytically dehydrogenated to cyclohexanone and a hydrogen containing gas, resulting in a second mixture containing cyclohexanol and cyclohexanone;
   the improvement comprising introducing said hydrogen containing gas from said dehydrogenation zone into a washing zone wherein said gas is washed with a washing liquid selected from the group consisting of cyclohexane and benzene, and the washed hydrogen containing gas thus obtained is fed into said hydrogenation zone.

2. The process of claim 1 wherein benzene is hydrogenated in said hydrogenation zone in the presence of a metal catalyst selected from the platinum group.

3. The process of claim 2 wherein benzene is hydrogenated in the presence of a catalyst containing platinum.

4. The process of claim 1 wherein the liquid used in said washing zone is cyclohexane, and the resulting washing liquid effluent from said zone is fed into the oxidation zone.

5. The process of claim 1 wherein said liquid used in said washing zone is cyclohexane, and the resulting washing liquid effluent is fed into a cyclohexane distillation zone wherein said first mixture containing cyclohexanol and cyclohexanone is also fed, and wherefrom cyclohexane is recovered by distillation.

* * * * *